United States Patent [19]
Arretz

[11] Patent Number: 5,877,349
[45] Date of Patent: Mar. 2, 1999

[54] PROCESS FOR THE SYNTHESIS OF 3-MERCAPTOPROPIONIC ACID

[75] Inventor: Emmanuel Arretz, Pau, France

[73] Assignee: Elf Acquitaine Exploration Production France, France

[21] Appl. No.: 933,840

[22] Filed: Sep. 19, 1997

[30] Foreign Application Priority Data

Sep. 20, 1996 [FR] France ................................. 96 11508
Jan. 31, 1997 [FR] France ................................. 97 01080

[51] Int. Cl.$^6$ .................................................. C07B 53/00
[52] U.S. Cl. ............................................................ 562/606
[58] Field of Search ............................................. 562/606

[56] References Cited

U.S. PATENT DOCUMENTS

| | | | |
|---|---|---|---|
| 3,346,516 | 10/1967 | Minton | 521/32 |
| 4,231,956 | 11/1980 | Sullivan, III et al. | 260/465.8 R |
| 5,008,380 | 4/1991 | Roberts | 558/436 |
| 5,028,259 | 7/1991 | Lin et al. | 75/722 |
| 5,340,380 | 8/1994 | Virnig | 75/744 |

FOREIGN PATENT DOCUMENTS

| | | |
|---|---|---|
| 208323 | 1/1987 | European Pat. Off. |
| 07228568 | 8/1995 | Japan . |
| 7-228568 | 8/1995 | Japan . |

OTHER PUBLICATIONS

Hino et al., Chemical Abstract No. 116667f, vol. 124, No. 9, pp. 1202, Aug. 1995.

French Search Report Dated Jun. 20, 1997.

"Preparation of a New o–Nitrobenzyl Resin for Solid–Phase Synthesis of tert–Butyloxycargonyl–Protected Peptide Acids", D.H. Rich et al., J.Am. Chem.Soc., 1975, vol 97, pp. 1575–1579.

"Preparation of Aminomethyl–Polystyrene Resin by Direct Amidomethylation", A.R. Mitchell, et al., Tetrahedron Letters, No. 42, 1976, pp. 3795–3798.

Chemical Abstracts, vol. 124, No. 9, p. 1202, No. 116667f, Y. Hino, et al.

"Polyurethane Sulfides Containing Cyclohexane Ring in the Polymer Chain", Iwakura, et al. Journal of Polymer Science, Part A, vol 2, 1964, pp. 881–883.

"New Macrohetrocyclic Systems –Derivatives Of 1, 2–Benzo–4, 13–Diaza–7,10–Dithiacyclotetradeca–1–Ene and 1,4–Diaza–7, 10,11,14–Tetrathiacyclohexadecane", M.G. Voronkov, et al., Chemical Heterocycl. Compd, vol. 15, 1979, pp. 1183–1185.

New Methods of Preparative Organic Chemistry VI, Synthesis of Isocyanates and Carbodiimides, H. Ulrich, et al., Agnew. Chem. Intern. Ed. Engl., vol. 5, 1966, pp. 704–712.

H. Bredereck, Chem. Ber., vol. 94, 1961, pp. 2278–2295 (no translation available).

"Amide chlorides and carbamide chlorides", H. Eilingsfeld, et al., Angew. Chem., vol. 72, pp. 836–845 w/Chem.Abs, vol. 66 (1961), p. 5321.

N,N,N'–Tetramethylchloroformamidinium Chloride As An Efficient Condensation Reagent For A Novel Esterification Aplicable To The Macrolide Synthesis, Fujisawa, et al., Chemistry Letters, 1982, pp. 1891–1894.

"Polumer–Supported Bases.XI, Esterification And Alkylation In The Presence Of Polymer–Supported Bicyclic Amidine Or Guanidine Moieties" J.M.S. Pure Appl. Chem., vol. A29(3), 1992, pp. 249–261, K.Iijimi, W. Fukada and M. Tomoi.

Primary Examiner—Samuel Barts
Assistant Examiner—Rosalynd Keys
Attorney, Agent, or Firm—Bell, Boyd & Lloyd

[57] ABSTRACT

This process for the synthesis of 3-mercaptopropionic acid by an addition reaction of $H_2S$ with acrylic acid is carried out in the presence of a solid support having basic guanidine functional groups, provided that the latter do not contain hydrogen bonded directly to a nitrogen atom.

11 Claims, 1 Drawing Sheet

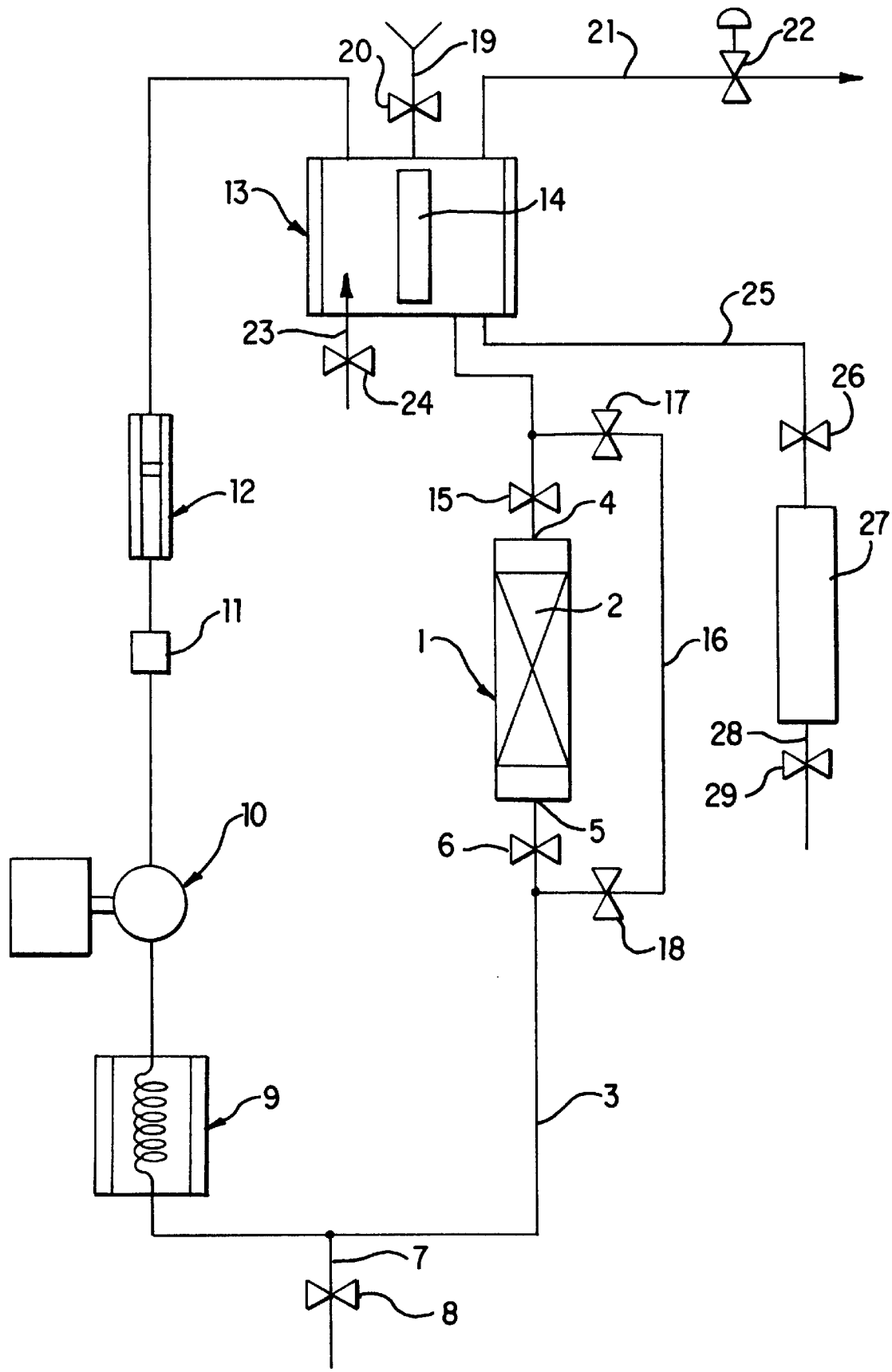

PROCESS FOR THE SYNTHESIS OF 3-MERCAPTOPROPIONIC ACID

FIELD OF THE INVENTION

The present invention relates to the preparation of 3-mercaptopropionic acid (MPA) by addition of hydrogen sulphide to acrylic acid (AA) according to the reaction (1):

$$H_2S + CH_2=CH-COOH \rightarrow HS-CH_2-CH_2-COOH \quad (1)$$

The MPA formed can react with the AA present in the reaction mixture to give 3,3'-thiodipropionic acid (TDPA) according to the reaction (2):

$$HS-CH_2-CH_2-COOH + CH_2=CH-COOH \rightarrow S(CH_2-CH_2-COOH)_2 \quad (2)$$

BACKGROUND OF THE INVENTION

U.S. Pat. No. 5,008,432 describes the addition of $H_2S$ to unsaturated compounds, such as methyl acrylate or acrylic acid.

This addition is carried out in the presence of a basic catalyst chosen from magnesium oxide and basic anion-exchange resins. These resins are chosen from those having tertiary amines or quaternary ammonium hydroxides as functional group.

The reaction takes place in the absence or in the presence of solvents. The latter are chosen from lower alcohols, saturated aliphatic or cycloaliphatic hydrocarbons and aromatic hydrocarbons.

If an anion-exchange resin is used, the reaction pressure is generally from 3037.5 to 6750 kPa.

Example VII describes the addition of $H_2S$ to acrylic acid, without solvent, at a reaction pressure of 3037.5 kPa, in the presence of Amberlyst A-21 resin (Rohm and Haas). This resin has dimethylamino functional groups. During the reaction, a solid separate from the liquid medium is formed. This solid contains mercaptans, sulphides, acrylic acid and dimers and trimers. Test No. 4 of this example would result, for an $H_2S/AA$ molar ratio of 10.4, in a conversion of 89% and a selectivity of 100% for MPA.

Test No. 3 would result, for an $H_2S/AA$ molar ratio of 5.4, in a conversion of 90% for a selectivity of 98% for MPA.

Patent application J07-228568 also relates to the synthesis of MPA by addition of $H_2S$ to acrylic acid. According to the process of this application, the addition is carried out in the presence of an anion-exchange resin and of a solvent chosen from water or amide, ester, ether or ketone compounds.

The amide, ester, ether or ketone solvent must not have a hydrogen bonded to an oxygen, sulphur, nitrogen and similar atom. Among the solvents which may be used in this process, dimethylformamide (DMF), dimethylacetamide, N-methylpyrrolidone and dimethylimidazolidinone are recorded among the amide solvents, DMF being preferred as it results in a high MPA yield.

Dioxane, dioxolane and diethylene glycol dimethyl ether are recorded among the ether solvents, dioxane being preferred as it results in a high MPA yield.

Acetone, diethyl ketone, methyl ethyl ketone and methyl isobutyl ketone are recorded among the ketones.

The anion-exchange resin described can have, as functional group, a tertiary amine (weakly basic resins) or a quaternary ammonium hydroxide (strongly basic resins). The weakly basic anion-exchange resins are indicated as ideal in practice because they do not form salts with the compounds of the reaction mixture.

The polymer of these resins, rendered insoluble by crosslinking, can be polystyrene, polyacrylamide or an epoxy resin.

In J07-228568, the examples of the synthesis of MPA employ the following resins manufactured by the company Rohm & Haas:

Amberlite IRA 93 (groups: tertiary amine)

Amberlite IRA 94 (groups: tertiary amine)

Amberlite IRA 900 (groups: quaternary ammonium)

Example 2 (Amberlite IRA 94 resin) and Example 12 (Amberlite IRA 900 resin), carried out under identical conditions as regards the molar ratio ($H_2S/AA=3$) and the reaction temperature of 60° C., would result virtually identical MPA yields (90.0% and 89.7%) and selectivities (90.6% and 90.8%).

Example 3, carried out in DMF in the presence of Amberlite IRA-94 resin, would result in a conversion of the AA of 98.9% and an MPA yield of 91.5% with a selectivity of 92.5%, for an $H_2S/AA$ molar ratio of 6.0, a reaction temperature of 60° C., a pressure of 30 atm (3039 kPa) and a maximum pressure of 44 atm (4458 kPa).

DESCRIPTION OF THE INVENTION

The aim of the present invention is to find conditions for the implementation of the reaction (1) such that, while retaining a very high degree of conversion, the selectivity for MPA is markedly better than that of the prior art, in particular that which could be obtained from the technical teaching of the document J07-228568.

This aim is achieved in the above reaction (1) by replacing the resins of the prior art by a solid support having guanidine functional groups, provided that the latter do not contain hydrogen bonded directly to a nitrogen atom.

The subject of the present invention is thus a process for the preparation of 3-mercaptopropionic acid by an addition reaction of $H_2S$ with acrylic acid in the presence of a solid support having basic functional groups, characterized in that the functional groups are guanidine groups, provided that the latter do not contain hydrogen bonded directly to a nitrogen atom.

The solid support can be any support which is insoluble in the reaction mixture. Mention may be made, as examples of such supports, of silica and alumina but it is preferable to use a polymeric support of any kind.

When the reaction (1) is carried out in the presence of a solvent, the polymeric support must additionally be substantially insoluble in the solvent. This insolubility is generally obtained by crosslinking the polymer or polymers constituting the polymeric support.

The present invention more specifically provides a process for the synthesis of 3-mercaptopropionic acid by an addition reaction of $H_2S$ with acrylic acid in the presence of a solid support having basic functional groups, characterized in that these functional groups are chosen from:

1) a guanidine radical of general formula (C):

in which $R_1$, $R_2$, $R_3$ and $R_4$ are, independently of one another, hydrocarbon groups such as methyl, ethyl, propyl or butyl, the imine nitrogen being bonded to the solid support via a chemical bond or a sequence of chemical bonds, 2) a bicyclic guanidine radical of formula (D):

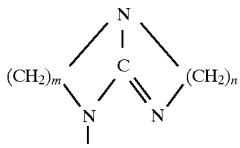

in which n has the value 2 or 3 and m has the value 2, 3 or 4, provided that n is less than or equal to m, this radical (D) being bonded to the solid support via a chemical bond or a sequence of chemical bonds starting from the initially N—H nitrogen of the corresponding bicyclic guanidine.

The radical (D) can advantageously be chosen from the $\Delta^8$-hexahydro-1,4,8-pyrimidazolyl (m=3, n=2), $\Delta^9$-1,5,9-triazabicyclo[4.4.0]decenyl (m=3, n=3), $\Delta^9$-1,4,9-triazabicyclo[5.3.0]decenyl (m=4, n=2) and 2,3,5,6-tetrahydro-1H-imidazo[1,2-a]-imidazolyl (m=2, n=2) radicals.

This process makes it possible to obtain, with an excellent degree of conversion of the AA, a better selectivity for MPA than the processes of the prior art, with in particular a concomitant decrease in the content of TDPA in the reaction mixture.

Thus, surprisingly, everything takes place as if the guanidine functional groups selectively increased the kinetics of the reaction (1) with respect to the kinetics of the reaction (2).

The increase in the selectivity for MPA of the process according to the present invention is based hereinbelow on the presentation of comparative examples including a quantitative calibration of chromatograms (see the experimental part).

The functionalized resin based on polystyrene-divinylbenzene (PS-DVB) preferably has the general formula (I):

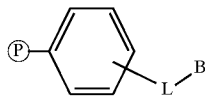

B being a group chosen from the radicals of general formula (c) or (D), L being a linear organic radical having a length equal to or greater than that of the methylene radical —(CH$_2$)— or the radical,

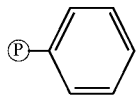

being the PS-DVB resin support.

Preferably, in the general formula (I):
  the radical (C) is substituted by L, the latter then representing a —CH$_2$— radical and $R_1$, $R_2$, $R_3$ and $R_4$ each representing a methyl group,
  the radical (D) is substituted by L on the nitrogen which, in the related bicyclic compound, carries a hydrogen, provided that L then represents a —(CH$_2$)$_p$— radical, p being an integer having a value from 1 to 9.

The functionalized polymeric resin advantageously has the general formula (II):

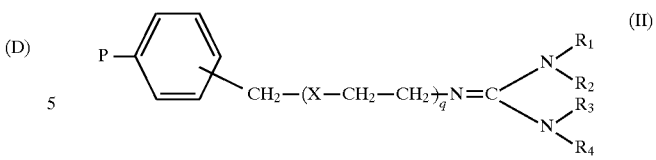

in which X represents an oxygen or sulphur atom, q has the value 1 or 2 and $R_1$, $R_2$, $R_3$ and $R_4$ are, independently of one another, chosen from the methyl, ethyl, propyl and butyl groups.

Advantageously, in the general formula (II), $R_1$, $R_2$, $R_3$ and $R_4$ each represent a methyl group and q has the value 1.

Preferably, the addition reaction (1) takes place in the presence of a solvent, the latter not having a mobile hydrogen.

In general, the said solvent is an amide, ester, ether or ketone solvent or one of their mixtures. The said solvent is advantageously chosen from dimethylformamide (DMF), diethylene glycol dimethyl ether or dioxane. The most preferred solvent is DMF.

The H$_2$S/AA molar ratio should preferably be high in order to promote the reaction (1) even more with respect to the reaction (2). This molar ratio is generally between 3 and 10.

It is preferable, in order to increase this molar ratio in the liquid mixture in contact with the solid resin acting as basic catalyst, to subject the reaction mixture to an H$_2$S pressure which is greater than atmospheric pressure. The pressure is generally greater than 15 bar (1500 kPa) and can reach 35 bar (3500 kPa) when the reaction is carried out at high temperatures.

The reaction is advantageously carried out at a temperature of 20° C. to 150° C. The temperature of the reaction mixture preferably ranges from 30° C. to 110° C.

The amount by weight of resin used with respect to the amount by weight of acrylic acid employed is advantageously from 1 to 100% and preferably from 10 to 70%.

The catalysts containing a guanidine functional group of the invention exhibit high chemical and thermal stability with respect to the reaction mixture and can thus be used continuously or reused without reactivation.

The reaction can be carried out in a stirred or tubular reactor, according to a non-continuous process, either by charging the reactants before they react or by gradual addition of acrylic acid after the addition of the hydrogen sulphide or alternatively by simultaneous addition of the reactants to the reactor, and, finally, according to a continuous process with controlled addition of the reactants.

The resins of general formula (I) can be obtained or prepared in the following way:

1) The group B is a radical of general formula (C).

A process is known, from U.S. Pat. No. 5,340,380, which consists in substituting the chlorine of a chloromethylated polystyrene-divinylbenzene resin with a substituted or unsubstituted guanidine and which makes it possible to obtain resins of general formula (I.C):

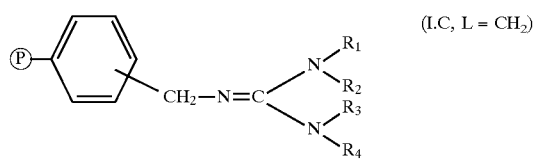

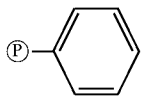

representing the starting polystyrenedivinylbenzene resin solid support and it being possible for the symbols $R_1$, $R_2$, $R_3$ and $R_4$ each to be a hydrogen, an alkyl group or an aromatic group.

U.S. Pat. No. 3,346,516 also describes this reaction of a chloromethylated polystyrenedivinylbenzene resin with guanidine or tetramethylguanidine in the presence of a lower alcohol and a solvent for swelling the PS-DVB copolymer, such as tetrahydrofuran, dioxane or diglyme.

In U.S. Pat. No. 5,028,259, tetramethylguanidine is brought into contact with a chloromethylated polystyrene-divinylbenzene resin in a mixture of toluene and tetrahydrofuran.

In U.S. Pat. No. 5,340,380, guanidines are reacted with this same type of chloromethylated resins in the presence of sodium hydroxide in a solvent composed of ethanol or of water.

However, this technique for functionalizing a chloromethylated PS-DVB resin with a guanidine is very limited in practice for the production of resins of formulae (I.C) in which the guanidine radicals carry $R_1$ to $R_4$ substituents which are other than four methyls, insofar as only 1,1,3,3-tetramethylguanidine is currently available commercially.

Such resins (I.C), in which the $R_1$ to $R_4$ groups are all other than hydrogen, can be obtained by using tetrasubstituted ureas, which are often available commercially, under the following preparation conditions:

a) The starting point is the preparation of a PS-DVB resin functionalized by primary amine groups having the general formula (A)

These can be obtained by different techniques:

1) It is possible, for example, to start from a resin of general formula (J):

X being a leaving group, in particular halogen or tosylate, obtained from a hydroxyl group —OH, and L representing in particular a —(CH$_2$)$_p$— radical with p being an integer having a value from 1 to 9.

Preferably, when L represents a single methylene, X is a chlorine atom. In this case, one method, described by D. H. Rich and S. K. Gurwara, J. Am. Chem. Soc., 1975, 97, 1575–1579, consists in reacting a chloromethylated PS-DVB resin with an excess of ammonia. Another route is based on obtaining phthalimidomethylated PS-DVB resin, which is converted by hydrazinolysis into a resin containing a primary amine functional group. The two methods of access to such phthalimidomethylated resins are described in the publication by A. R. Mitchell, S. B. H. Kent, B. W. Erickson and R. E. Merrifield, Tetrahedron Letters, No. 42, 1976, 3795–3798. One consists in starting from a PS-DVB resin which, by reaction with N-(chloromethyl)phthalimide, is directly converted into phthalimidomethylated resin. The other method starts from a chloromethylated PS-DVB resin, which is treated with potassium phthalimide in order to give the corresponding phthalimidomethylated resin.

A few PS-DVB resins containing a primary amine functional group of formula (A) in which L represents a methylene are commercially available.

Thus, the Company Purolite provides two macroporous resins, A-107 and A-109, while the Company Fluka has, in its 1995–1996 catalogue, two gel-type resins: the resin 08564 PS, crosslinked with 2%. DVB and containing 1.1 mmol of —NH$_2$ groups per gram of resin, and the resin 08566 PS, crosslinked with 1% DVB and containing 0.6 mmol of —NH$_2$ per gram of resin.

The potassium phthalimide method is also applicable to the resins of formula (J) in the case where L is a linear organic radical with a length greater than that of the methylene radical, in particular —(CH$_2$)$_r$— with r having the value of an integer greater than 1.

2) It is also possible to start from a PS-DVB resin of formula (J) in which L represents a methylene and X has the above meaning and preferably represents a chlorine atom. Applicant has found that this chloromethylated resin can be reacted with an alkanolamine or a mercaptoalkylamine, in the form of an alkali metal alkoxide or thiolate, under the conditions of the Williamson reaction.

If ethanolamine is employed, PS-DVB resins containing a primary amine functional group are obtained with —CH$_2$—O—CH$_2$—CH$_2$—NH$_2$ functional groups attached to the PS-DVB resin supports.

Analogously, starting from 2-aminoethanethiol hydrochloride, —CH$_2$—S—CH$_2$—CH$_2$—NH$_2$ functional groups are obtained.

If 2-(2-aminoethoxy)ethanol is used, PS-DVB resins containing a primary amine functional group are obtained with —CH$_2$(—O—CH$_2$—CH$_2$)$_2$—NH$_2$ functional groups.

Finally, by using 2-[(2-aminoethyl)thio]-ethanethiol, the functional groups obtained are:

—CH$_2$—(S—C$_2$—CH$_2$)$_2$—NH$_2$.

This starting mercaptoalkylamine can be prepared according to Iwakura et al., J. Polym. Sci., Part A, 2, 1964, 881–883, or according to Voronkov, M. G. et al., Chem. Heterocycl. Compd. (Engl. Transl.), 15, 1979, 1183–1185.

The general conditions of the Williamson reaction are as follows:

The alkanolamine or the mercaptoalkylamine, diluted in anhydrous tetrahydrofuran (THF) or anhydrous N-methylpyrrolidone, is reacted with sodium hydride in suspension in the same anhydrous solvent. After formation of the sodium alkoxide or sodium thiolate, the chloromethylated resin is introduced into the liquid reaction mixture.

b) After obtaining the resin possessing primary amine groups of general formula (A), these primary amine groups are reacted with chloroformamidinium chloride (Vilsmeier salt) of general formula (H):

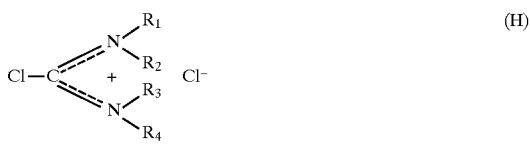

in which $R_1$, $R_2$, $R_3$ and $R_4$ are, independently of one another, chosen from the methyl, ethyl, propyl and butyl groups, in order to obtain a PS-DVB resin functionalized by a guanidine group and with the general formula (I.C):

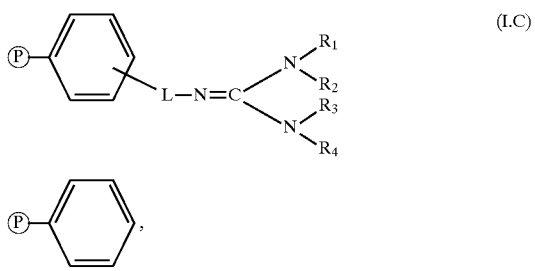

L and $R_1$ to $R_4$ having the same meanings as above.

The chloroformamidinium chlorides (H) are generally obtained from tetrasubstituted ureas by reaction with electrophilic compounds, such as phosgene, thionyl chloride, oxalyl chloride or phosphorus oxychloride, according to methods described in the literature, in particular:

$COCl_2$ H. Eilingsfeld, M. Seefelder, Angew. Chem., 72, 1960, 836.

$SOCl_2$ H. Ulrich, A. A. R. Sayigh, Angew. Chem. Intern. Ed. Engl., 5, 1966, 704.

($COCl_2$ T. Fujisawa et al., Chem. Lett., 1982, 1891.

$POCl_3$ H. Bredereck, K. Bredereck, Chem. Ber., 94, 1961, 2278.

The starting point is generally stoichiometric amounts of tetrasubstituted ureas and of electrophilic chlorinated compounds and the reaction is carried out in the presence of a solvent, such as carbon tetrachloride, in the case of oxalyl chloride, or without a solvent, with phosgene or thionyl chloride, at a temperature generally of 0° C. to 40° C. and in an anhydrous atmosphere, in order to avoid any hydrolysis.

The tetrasubstituted ureas are advantageously chosen from tetramethylurea, tetraethylurea, tetra(n-propyl)urea and tetra(n-butyl)urea.

The chloroformamidinium chlorides (H) are generally placed in a solvent, such as toluene or acetonitrile. Their reactions with the resins containing a primary amine functional group (A) are carried out in the presence of a base, preferably in the presence of an excess of base.

If the base is triethylamine (TEA), the reaction is generally carried out with a molar excess of TEA of 10 to 50% with respect to the chloroformamidinium chlorides (H). The latter are generally in a molar excess of 10 to 100% with respect to the number of moles of primary amine functional group, in order to convert all of the latter into a guanidine functional group.

2) In the general formula (I), the group B is a radical of formula (D)

(a) The starting point is the preparation of a resin of general formula (J), as in part 1 a) above, L representing a $-(CH_2)_p-$ radical, p being an integer having a value from 1 to 9, and X being a chlorine or a bromine.

(b) The above halogenated resin is reacted with a bicyclic guanidine chosen in particular from $\Delta^8$-hexahydro-1,4,8-pyrimidazole (m=3, n=2), $\Delta^9$-1,5,9-triazabicyclo[4.4.0]decene (TBD) (m=3, n=3), $\Delta^9$-1,4,9-triazabicyclo[5.3.0]decene (m=4, n=2) and 2,3,5,6-tetrahydro-1H-imidazo[1,2-a]imidazole (m=2, n=2).

The preparation of these bicyclic guanidines is described in Patents GB 826,837 and EP 0,198,680.

The reaction is carried out in a way analogous to the process of M. Tomoi et al., J. M. S. Pure Appl. Chem., A29(3), 1992, 249–261, in particular page 251 ("Preparation of Polystyrene-Supported TBD").

A PS-DVB resin functionalized by a bicyclic guanidine group is thus obtained of general formula (I.D):

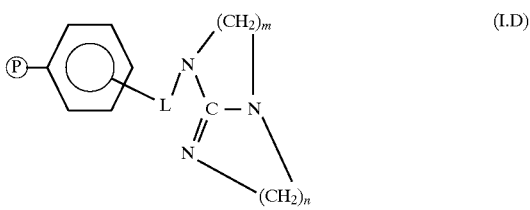

L representing a $-(CH_2)_p-$ radical with p being an integer having a value from 1 to 9.

The process of Tomoi et al., J. Macromol. Sci. Pure Appl. Chem., A29(3), 1992, 249–261, consists in reacting the lithium salt of TBD with a chloromethylated resin. A simplified procedure was studied in the context of the present invention in order to prepare larger amounts of resins containing a -TBD functional group, by reacting excess 1,5,7-triazabicyclo[4.4.0]dec-5-ene directly with chloromethylated PS-DVB resin in anhydrous THF as solvent.

The catalytic effectiveness of the resins used in the present invention is found to be improved when they are used dry.

EXAMPLES

The present invention will be better understood by virtue of the experimental part hereinbelow which in particular comprises a description of the equipment used, the latter being represented diagrammatically in the single appended figure.

Experimental Part

I. Preparation of polystyrene-divinylbenzene resins containing a guanidine functional group.

The chloromethylated PS-DVB base resin which is used is of macroporous type. It has the following characteristics:

Specific surface: 22.5 $m^2$/g of resin

Mean pore diameter: 20 Å

Volume of the pores: 69% chloromethylated with a degree of chlorine of 19.32% by weight with respect to the total weight.

This resin thus contains 5.44 meq of Cl/g of resin.

I.1 Production of PS-DVB resins of formula (I.C) containing a 1,1,3,3-tetramethylguanidine (TMG) functional group, $(L=-CH_2-, R_1=R_2=R_3=R_4=CH_3-)$ The technique used consists in incorporating the TMG directly in a chloromethylated PS-DVB resin, according to the method described in U.S. Pat. Nos. 3,346,516 and 5,028,259.

Procedure:

20 g of dry chloromethylated resin (5.44 meq of Cl/g of resin) are weighed out. It contains 0.109 mol of Cl. It is brought into contact, under a nitrogen atmosphere, with 50 g (0.435 mol) of TMG diluted in 210 g of tetrahydrofuran (THF) dried beforehand over a molecular sieve. The reaction mixture thus obtained is stirred mechanically for 48 hours at a temperature of 60° C. After cooling to 20° C., the resin is filtered off and is washed with 500 ml of water and then with 250 ml of water at 60° C. It is then treated with 300 ml of a 10% aqueous sodium hydroxide solution and washed with water to neutrality. The resin is washed with methanol (300 ml) and then dried under vacuum at 60° C. to constant weight.

The elemental analysis of the resin thus obtained was carried out. For this resin, N=9.3% by weight, i.e. 2.2 mmol of TMG functional group/g of resin.

Resin subsequently indicated: PS-DVB-TMG

I.2 Production of PS-DVB resins of formula (I.D) containing a 1,5,7-triazabicyclo[4.4.0]dec-5-ene (TBD) functional group with L=—$CH_2$—.

Procedure:

20 g of dry chloromethylated resin (5.44 meq of Cl/g of resin) are weighed out. The resin charge contains 0.109 mol of Cl. It is brought into contact, under a nitrogen atmosphere, with 30 g (0.216 mol) of TBD diluted in 285 g of THF dried beforehand over a molecular sieve. The reaction mixture thus obtained is stirred mechanically for 48 hours at a temperature of 60° C. After cooling to 20° C., the resin is filtered off and is washed with 500 ml of water and then 250 ml of water at 60° C. It is then treated with 300 ml of a 10% aqueous sodium hydroxide solution and washed with water to neutrality. The resin is washed with methanol (300 ml) and then dried under vacuum at 60° C. to constant weight.

The elemental analysis of the resin thus obtained was carried out. For this resin, N=13.26% by weight, i.e. 3.15 mmol of TBD functional group/g of resin.

Resin subsequently indicated: PS-DVB-TBD

II. Examples of the synthesis of 3-mercaptopropionic acid

II.1. General points

The tests were carried out in equipment which makes it possible to study, under pressure, the formation reaction of 3-mercaptopropionic acid from acrylic acid and hydrogen sulphide in a solvent (dimethylformamide or diglyme) with different basic resins as catalysts.

The introduction of the reactants and of the solvent before the start of the reaction makes it possible to carry out the reaction according to a batch process (the progress of the reaction is equivalent to continuous plug-flow operating conditions).

The design of the equipment (description of the equipment: paragraph II.2) makes it possible to study the reaction under stirred batch conditions (closed reactor) by means of a tubular reactor (resin in a stationary bed), through which recirculates, at a high flow rate, the liquid reaction mixture via a pump on the circuit of a circulation loop which is connected to the two ends of the reactor.

This operating technique of stirred batch type makes it possible to study the kinetics of the reaction under conditions which are equivalent to continuous plug-flow operating conditions (open reactor), given that all the reactants ($H_2S$ and acrylic acid) are introduced, as well as the solvent, into the equipment before the start of the reaction, the reactor being isolated (no contact with the resin) (operating protocol: paragraph II.3).

The progress of the reaction with time is monitored by withdrawing samples which are analysed by gas chromatography in order to determine the conversion of the acrylic acid and the corresponding selectivities for 3-mercaptopropionic acid and for 3,3'-thiodipropionic acid as a function of time.

BRIEF DESCRIPTION OF THE DRAWING

II.2. Equipment

As represented in the single figure, the stainless steel equipment is composed of the following elements:

a vertical tubular reactor 1, in which the functionalized resin charge 2 is contained, a recirculation loop 3 which emerges at the upper end 4 and at the lower end 5 of the reactor 1, this loop comprising pipes successively connecting, from the lower end 5, a closing valve 6, a by-pass 7 equipped with a valve 8, a jacketed exchanger 9, a gear pump 10 (maximum throughput 40 l/h), a temperature recorder 11, a ball flowmeter 12 and a jacketed cylindrical tank 13 equipped with a window 14 made of thick transparent glass. This tank 13 is connected to the upper end 4 of the reactor via a pipe which passes through a closing valve 15. The tank 13 is placed above the reactor 1.

This circulation loop 3 itself contains a bypass loop 16 equipped with 2 valves 17 and 18.

This loop 16 makes it possible to isolate the reactor 1 from the circulation stream by virtue of the interaction of the valves 6, 15, 17 and 18.

The tank 13 is equipped, at its upper part, with a pipe 19 for introducing acrylic acid and the various solvents. This pipe 19 containes a valve 20. The tank 13 is also equipped with a pipe 21 equipped with a pressure valve 22. The pipe 21 is connected to a flare.

The tank 13 is equipped, at its lower part, with a pipe 23 equipped with a valve 24, which pipe is intended for the introduction of pressurized $H_2S$ into the tank.

The lower part of the tank is connected, via a pipe 25 equipped with a valve 26, to a receiver 27. The latter is equipped, at its lower part, with a pipe 28 equipped with a valve 29. The pipe 28 makes it possible to recover samples during reaction.

II.3. Operating protocol

The operations of charging resin and of introducing acrylic acid and the solvent are carried out in a nitrogen atmosphere.

II.3.1 Preparation of the Reaction Mixtures

The reactor 1, containing the resin 2 (charges of the order of 20 g), is isolated from the rest of the equipment by closing the valves 6 and 15. The acrylic acid and the solvent are introduced via the pipe 19 into the cylindrical tank 13 which is in direct communication with the recirculation loop. The equipment is pressurized to a pressure of 3 bar of nitrogen. The cylindrical tank 13, in which the starting reaction mixture will be prepared, is cooled by circulating oil at 12° C. (originating from a cryostat) which also passes through the external jacket of the exchanger 9 of the recirculation loop. The circulation pump 10 is started and the liquid contained in the cylindrical tank circulates in the loop 3 and the loop 16 by being directed from the tank 13 towards the valve 17 before passing through the valve 18.

The hydrogen sulphide, supplied under a pressure of 16 bar, is injected via the pipe 23 into the tank 13 by means of a diffuser and dissolves in the cooled liquid mixture (at the start: acrylic acid+solvent). At the end of the injection of the $H_2S$, the pressure is 15 bar and the temperature of the liquid mixture (acrylic acid+$H_2S$+solvent) is 20° C. The charging volume can be controlled via the window 14.

II.3.2 Performing the Tests

The cryostat set point is placed at the value corresponding to the temperature at which the reaction has to be carried out and, while the oil rapidly rises to the set temperature, the circulating reaction mixture is introduced, by opening the valves 15 and 6 and closing the valves 17 and 18, into the reactor 1, through which it recirculates at a high flow rate (maximum: 40 l/h). The reaction temperature programmed for the test is maintained throughout the duration of the reaction, i.e. generally 6 hours. The pressure of the gas phase in the plant, which is connected to the pressure valve 22, becomes established between 19 bar and 24 bar, depending on the test conditions.

During testing, samples of the reaction mixture are withdrawn at predetermined times via the receiver 27 and recovered at atmospheric pressure and are then analysed by gas chromatography. At the end of the test, the plant is decompressed and the final reaction product is recovered.

II.4. Analysis of the reaction products

Analysis by gas chromatography (GC) required a specific development in order to solve the problems posed by the analysis of 3,3'-thiodipropionic acid and by the separation of acrylic acid and dimethylformamide.

3,3'-Thiodipropionic acid, because of its physical properties and its polar functional groups, can only be analysed at high temperature with a chromatographic column of high thermal stability (greater than 300° C.) and of very low polarity. The chromatography columns which may be suitable are capillary columns containing polysiloxane-based phases; the non-polar crosslinked dimethylpolysiloxane phase is very well suited. This type of phase is not appropriate for the separation of acrylic acid and dimethylformamide with columns commonly used in laboratories, that is to say 25-meter or 50-meter columns. The separation of these two compounds could be obtained by connecting two, respectively 50 m and 25 m, Hewlett Packard Ultra-1 capillary columns in series, the chromatography device being a Hewlett Packard 5890 FID.

The results of the chromatographic analyses of the reaction samples were controlled by analyses of reference samples of known compositions by weight, prepared from acrylic acid (AA), 3-mercaptopropionic acid (MPA), 3,3'-thiodipropionic acid (TDPA) and solvent (DMF or diglyme). These control analyses have made it possible to determine the response factors relating to the various constituents. In the case of the evaluation of the content of 3,3'-thiodipropionic acid, its true content in the samples is greatly reduced when analysed by GC and a specific correction is essential in order to determine quantitatively the 3,3'-thiodipropionic acid produced in the reaction.

II.5. Experimental tests

II.5.1 General Points

The tests were carried out according to the operating protocol which has been employed by us and which has been described in a preceding paragraph. Withdrawals from the reaction mixture were carried out at predetermined times in each test: after 2 hours, 4 hours and 6 hours.

The samples withdrawn were analysed by gas chromatography with the method which has been developed. These analyses give the value of the conversion of the acrylic acid (AA) at the predetermined times (2 h, 4 h and 6 h) and the selectivity by weight for 3-mercaptopropionic acid (MPA) and for 3,3'-thiodipropionic acid (TDPA).

II.5.2 Comparative Tests with the IRA 94 Resin and DMF

Comparative Test No. 1

The operating conditions taken for this test correspond to Example 2 of J07,228,568:

| Charge of IRA 94 resin | 24 g |
|---|---|
| DMF | 150 g |
| Acrylic acid | 100 g (1.39 mol) |
| $H_2S$ | 142 g (4.2 mol) |
| Molar ratio | $H_2S/AA = 3/1$ |
| Temperature | 60° C. |

At the reaction temperature of 60° C., the pressure in the equipment is 20 bar (relative).

Comparative Test No. 2

The operating conditions taken for this test correspond to Example 3 of J07,228,568:

| Charge of IRA 94 resin | 24 g |
|---|---|
| DMF | 150 g |
| Acrylic acid | 100 g (1.39 mol) |
| $H_2S$ | 284 g (8.34 mol) |
| Molar ratio | $H_2S/AA = 6/1$ |
| Temperature | 60° C. |

At the reaction temperature of 60° C., the pressure in the equipment is 24 bar.

II.5.3 Tests with the PS-DVB-TMG and DMF

Test No. 3

With the exception of the resin employed, the operating conditions of this test are identical to those used for Test No. 1:

| Charge of PS-DVB-TMG resin | 19 g |
|---|---|
| DMF | 150 g |
| Acrylic acid | 100 g (1.39 mol) |
| $H_2S$ | 142 g (4.2 mol) |
| Molar ratio | $H_2S/AA = 3/1$ |
| Temperature | 60° C. |

At the reaction temperature of 60° C., the pressure in the equipment is 19–20 bar (relative).

Test No. 4

With the exception of the resin employed, the operating conditions of this test are identical to those used for Test No. 2:

| Charge of PS-DVB-TMG resin | 19 g |
|---|---|
| DMF | 150 g |
| Acrylic acid | 100 g (1.39 mol) |
| $H_2S$ | 284 g (8.34 mol) |
| Molar ratio | $H_2S/AA = 6/1$ |
| Temperature | 60° C. |

At the reaction temperature of 60° C., the pressure in the equipment is 23–24 bar.

II.5.4 Tests with the PS-DVB-TMG Resin with Diglyme as Solvent

Test No. 5

This test was carried out under conditions identical to those of Test No. 3, with the sole difference that diglyme replaces DMF as solvent:

| PS-DVB-TMG resin | 19 g |
|---|---|
| Diglyme | 150 g |
| Acrylic acid | 100 g (1.39 mol) |
| $H_2S$ | 142 g (4.2 mol) |
| Molar ratio | $H_2S/AA = 3/1$ |
| Reaction temperature | 60° C. |

At the temperature of 60° C., the pressure in the equipment is 20 bar (relative).

Test No. 6

This test was carried out under conditions identical to those of Test No. 4, with the sole difference that diglyme replaces DMF as solvent:

| PS-DVB-TMG resin | 19 g |
|---|---|
| Diglyme | 150 g |
| Acrylic acid | 100 g (1.39 mol) |
| $H_2S$ | 284 g (8.34 mol) |

-continued

| Molar ratio | H₂S/AA = 6/1 |
|---|---|
| Reaction temperature | 60° C. |

At the temperature of 60° C., the pressure in the equipment is 24 bar (relative).

The results of Tests No. 3 and No. 4 (resin containing TMG guanidine functional group), compared with the results of Tests No. 1 and No. 2 (IRA 94 resin containing a tertiary amine functional group), show that the PS-DVB-TMG resin is markedly more selective than the IRA 94 resin for the production of 3-mercaptopropionic acid.

After 6 hours, with a charge of PS-DVB-TMG resin (19 g) which is lower than with the IRA 94 resin, comparable levels of conversion of the acrylic acid (AA) are obtained.

The same effects on the selectivity for 3-mercaptopropionic acid are encountered as a function of the H₂S/AA ratio, that is to say, from a 3/1 ratio to a 6/1 ratio, the gain in selectivity for MPA is comparable.

The results with the PS-DVB-TMG resin on using diglyme as solvent (Tests No. 5 and No. 6) are markedly poorer than with dimethylformamide (Tests No. 3 and No. 4). In diglyme, the conversion of the acrylic acid is much slower and the selectivity for 3-mercaptopropionic acid is significantly lower than in DMF.

DMF is a remarkable solvent which has the effect of greatly increasing the activity and the selectivity of the PS-DVB-TMG resin for the above reaction (1).

The conversion and selectivity values in the above Tests 1 to 6 and in the following tests are quantitative because they have been calibrated by reference mixtures.

If chromatographic response factors are not taken into account, an apparent selectivity for MPA of 80.4% (instead of the true 68.4%) and for TPDA of 19.3% (instead of the true 31.2%) are obtained for Test No. 1.

Likewise, Test No. 2 results in an apparent selectivity for MPA of 90.9% (instead of 84.1%) and an apparent selectivity for TDPA of 9.9% (instead of 15.8%).

The results obtained for the above tests are presented in the following Table I.

II.5.5 Comparative Tests in DMF as Solvent, at a Temperature 40° C., of Resins Containing Guanidine Functional Groups (Invention) and of Resins Containing a Tertiary Amine Functional Group.

These tests were carried out at a lower temperature with the aim of comparing the catalytic activities of the resins containing a guanidine functional group and of the resins containing an amine functional group under kinetic conditions which are more favourable for the production of 3-mercaptopropionic acid.

Two series of tests were carried out under identical operating conditions, with H₂S/acrylic acid molar ratios of 3/1 and 6/1, from 100 g (1.39 mol) of acrylic acid and 150 g of DMF (solvent).

Two resins containing a tertiary amine functional group were tested:

*IRA 94 (24 g), Rohm and Haas resin given as example in J07,228,568 and used as reference resin in our preceding tests.

*A-21 (22.5 g), Rohm and Haas resin given as example in U.S. Pat. No. 5,008,432 (or EP 208,323).

Two resins containing a guanidine functional group of the invention were tested:

*PS-DVB-TBD (21.6 g), resin containing our 1,5,7-triazabicyclo[4.4.0]dec-5-ene functional group, prepared according to the procedure described above.

*PS-DVB-TMG (19 g), resin containing a 1,1,3,3-tetramethylguanidine functional group, prepared according to the procedure described above.

Tests No. 7, 8, 9 and 10 with a molar ratio $$\frac{H_2S}{AA} = \frac{3}{1}$$

Conditions:

DMF: 150 g
Acrylic acid: 100 g (1.39 mol)
H₂S: 142 g (4.2 mol)

At the reaction temperature of 40° C., the pressure in the equipment is 17 bar (relative).

TABLE I

| Test No. | Solvent | H₂S/AA | 2 Hours ||| 4 Hours ||| 6 Hours |||
| | | | AA Conv. (%) | MPA Sel. (%) | TDPA Sel. (%) | AA Conv. (%) | MPA Sel. (%) | TDPA Sel. (%) | AA Conv. (%) | MPA Sel. (%) | TDPA Sel. (%) |
|---|---|---|---|---|---|---|---|---|---|---|---|
| 1* | DMF | 3/1 | 89.8 | 70.9 | 28.8 | 95.7 | 70.4 | 29.3 | 98.6 | 68.4 | 31.2 |
| 2* | DMF | 6/1 | 95.5 | 84.5 | 15.3 | 97.6 | 84.2 | 15.6 | 99.0 | 84.1 | 15.8 |
| 3 | DMF | 3/1 | 79.1 | 89.7 | 10.1 | 89.0 | 86.6 | 13.3 | 97.7 | 86.5 | 13.4 |
| 4 | DMF | 6/1 | 85.5 | 94.7 | 5.2 | 94.6 | 92.9 | 7.0 | 98.2 | 92.5 | 7.4 |
| 5 | Diglyme | 3/1 | 41.3 | 92.6 | 7.2 | 58.3 | 78.9 | 20.9 | 76.9 | 77.3 | 22.5 |
| 6 | Diglyme | 6/1 | 61.6 | 88.3 | 11.5 | 78.3 | 86.9 | 12.9 | 89.3 | 85.8 | 14.0 |

*Comparative Test

Tests No. 11, 12, 13 and 14 with a molar ratio

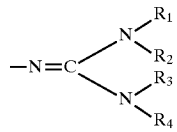

Conditions:
 DMF: 150 g
 Acrylic acid: 100 g (1.39 mol)
 H$_2$S: 284 g (8.34 mol)
 At the reaction temperature of 40° C., the pressure in the equipment is 20 bar (relative).
 The results obtained at 40° C. confirm the results of the preceding tests at 60° C. with the solvent DMF, namely:
 *The resins containing a guanidine functional group are more selective for 3-mercaptopropionic acid than the resins containing a tertiary amine functional group.
 In the case of the resins containing a guanidine functional group:
 *The decrease in temperature from 60° C. to 40° C. slightly improves the selectivity for 3-mercaptopropionic acid. In contrast, the decrease in temperature affects the rate of conversion of the acrylic acid.
 In the case of the resins containing a tertiary amine functional group:
 *The decrease in temperature from 60° C. to 40° C. has the same effects as for the guanidine resins (slight gain in selectivity for MPA and fall in the conversion of the acrylic acid).
 *The A-21 resin, which is more active than the IRA 94 resin, has the same selectivity for 3-mercaptopropionic acid as the IRA 94 resin.
 The results obtained for the 8 resins tested under these conditions are recorded in Table II.

TABLE II

| | | 2 Hours | | | 4 Hours | | | 6 Hours | | |
|---|---|---|---|---|---|---|---|---|---|---|
| Test No. | Resin | AA Conv. (%) | MPA Sel. (%) | TDPA Sel. (%) | AA Conv. (%) | MPA Sel. (%) | TDPA Sel. (%) | AA Conv. (%) | MPA Sel. (%) | TDPA Sel. (%) |
| 7* | IRA 94 | 66.9 | 78.2 | 21.6 | 82.5 | 77.8 | 22.0 | 92.5 | 76.9 | 22.9 |
| 8* | A-21 | 81.5 | 78.6 | 21.2 | 93.7 | 77.9 | 21.9 | 97.6 | 75.9 | 23.9 |
| 9 | PS-DVB-TBD | 80.6 | 88.7 | 11.2 | 90.9 | 87.2 | 12.7 | 96.2 | 86.8 | 13.1 |
| 10 | PS-DVB-TMG | 61.1 | 93.6 | 6.3 | 78.5 | 91.3 | 8.6 | 88.3 | 89.2 | 10.7 |
| 11* | IRA 94 | 68.1 | 87.0 | 12.8 | 85.6 | 85.0 | 14.8 | 95.1 | 84.2 | 15.6 |
| 12* | A-21 | 84.1 | 85.6 | 14.2 | 90.5 | 84.5 | 15.3 | 97.4 | 84.1 | 15.7 |
| 13 | PS-DVB-TBD | 86.0 | 94.5 | 5.4 | 93.8 | 93.8 | 6.1 | 96.8 | 92.8 | 7.1 |
| 14 | PS-DVB-TMG | 65.1 | 96.4 | 3.5 | 86.2 | 96.2 | 3.7 | 94.1 | 93.7 | 6.2 |

*Comparative Test

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:
 1. Process comprising the synthesis of 3-mercaptopropionic acid by an addition reaction of H$_2$S with acrylic acid in the presence of a solid support having basic functional groups, the functional groups are guanidine groups, provided that the latter do not contain hydrogen bonded directly to a nitrogen atom wherein the selectivity of 3-mercaptopropionic acid is substantially increased compared to processes using resins with dimethylamino tertiary amine or quaternary ammonium functional groups.
 2. Process according to claim 1, wherein these guanidine groups are selected from:
 1) a guanidine radical of formula (C):

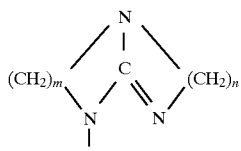

in which $R_1$, $R_2$, $R_3$ and $R_4$ are, independently of one another, hydrocarbon groups selected from methyl, ethyl, propyl or butyl, the imine nitrogen being bonded to the solid support via a chemical bond or a sequence of chemical bonds,
 2) a bicyclic guanidine radical of formula (D):

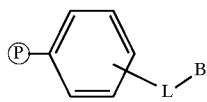

in which n has the value 2 or 3 and m has the value 2, 3 or 4, provided that n is less than or equal to m, this radical (D) being bonded to the solid support via a chemical bond or a sequence of chemical bonds starting from the initially N-H nitrogen of the corresponding bicyclic guanidine.
 3. Process according to claim 2, wherein the radical (D) is selected from the $\Delta^8$-hexahydro-1,4,8-pyrimidazolyl (m=3, n=2), $\Delta^9$-1,5,9-triazabicyclo(4.4.0)decenyl (m=3, n=3), $\Delta^9$-1,4,9-triazabicyclo(5.3.0)decenyl (m=4, n=2) and 2,3,5,6-tetrahydro-1H-imidazo(1,2-a)imidazolyl (m=2, n=2) radicals.
 4. Process according to claim 2, wherein the solid support is a resin based on polystyrene-divinylbenzene (PS-DVB) having the formula (I):

(I)

B being a group selected from the radicals of formula (C) or (D), L being a linear organic radical having the length equal to or greater than that of the methylene radical —(CH$_2$)— or the radical,

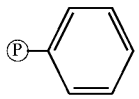

being the PS-DVB resin support.

5. Process according to claim 4, wherein:
   the radical (C) is substituted by L, the latter then representing a —CH$_2$— radical and R$_1$, R$_2$, R$_3$ and R$_4$ each representing a methyl group, or
   the radical (D) is substituted by L on the nitrogen which, in the related bicyclic compound, carries a hydrogen, provided that L then represents a —(CH$_2$)$_p$— radical, p being an integer having a value from 1 to 9.

6. Process according to claim 4, wherein the polymeric resin has the formula (II):

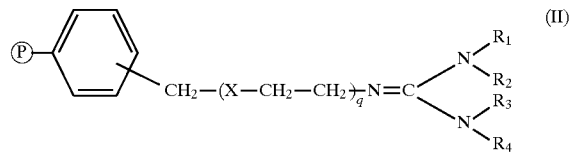

in which X represents an oxygen or sulphur atom, q has the value 1 or 2 and R$_1$, R$_2$, R$_3$ and R$_4$ are, independently of one another, selected from the methyl, ethyl, propyl and butyl groups.

7. Process according to claim 6, wherein R$_1$, R$_2$, R$_3$ and R$_4$ each represent a methyl group and q has the value 1.

8. Process according to claim 1, wherein the addition reaction takes place in the presence of a solvent, the latter not having a mobile hydrogen.

9. Process according to claim 8, wherein the said solvent is an amide, ester, ether or ketone solvent or one of their mixtures.

10. Process according to claim 9, wherein the said solvent is selected from dimethylformamide (DMF), diethylene glycol dimethyl ether or dioxane.

11. Process according to claim 10, wherein the said solvent is DMF.

* * * * *